United States Patent [19]

Shin

[11] 4,289,906

[45] Sep. 15, 1981

[54] CHEMICAL PROCESS FOR PREPARING METHYLENE BIS-ANILINES

[75] Inventor: Kju H. Shin, Bloomfield Hills, Mich.

[73] Assignee: Ethyl Corporation, Richmond, Va.

[21] Appl. No.: 101,544

[22] Filed: Dec. 10, 1979

[51] Int. Cl.$^3$ .............................................. C07C 85/02
[52] U.S. Cl. ..................................... 564/330; 564/496
[58] Field of Search ..................... 260/570 D; 564/330

[56] References Cited

U.S. PATENT DOCUMENTS

| | | | |
|---|---|---|---|
| 3,297,759 | 1/1967 | Curtiss et al. | 260/570 |
| 3,478,099 | 11/1969 | Ross et al. | 260/570 |
| 3,496,229 | 2/1970 | Powers et al. | 260/570 |
| 3,954,867 | 5/1976 | Funk, Jr. et al. | 260/570 |

OTHER PUBLICATIONS

Fieser et al.,"Reagents for Organic Synthesis", vol. II, p. 161, (1969).

Primary Examiner—Robert V. Hines
Attorney, Agent, or Firm—Donald L. Johnson; John F. Sieberth; Joseph D. Odenweller

[57] ABSTRACT

Aromatic amine hydrochloride having an unsubstituted ortho or para position reacts with dimethylsulfoxide forming methylenebis aromatic amine.

7 Claims, No Drawings

CHEMICAL PROCESS FOR PREPARING METHYLENE BIS-ANILINES

BACKGROUND OF THE INVENTION

Methylenebis aromatic amines are valuable chemicals. They have been used as antioxidants and as polyurethane intermediates. They are conventionally made by reacting the aromatic amine with formaldehyde and HCl. In this process the formation of chloromethylether presents a hazzard due to its toxicity.

The reaction of aniline hydrobromide with dimethyl sulfoxide has been reported to form mainly p-bromoaniline plus small amounts of o-bromoaniline (J. Org. Chem. 40, 1867 (1975)).

SUMMARY

It has now been discovered that when an aromatic amine hydrochloride having an unsubstituted ortho and/or para position is reacted with dimethylsulfoxide the main product is a methylenebis aromatic amine rather than the chloro aromatic amine that might be expected from the prior art.

DESCRIPTION OF THE PREFERRED EMBODIMENTS

A preferred embodiment of the invention is a process for making a methylenebisaniline, said process comprising reacting an aromatic amine having an unsubstituted ortho or para position with hydrogen chloride and dimethylsulfoxide.

Aromatic amines useful in the process have an unsubstituted ortho or para position. Examples of these include o-ethylaniline, 2,4-diethylaniline, o-toluidine, m-toluidine, p-toluidine, p-ethylaniline, o-isopropylaniline, 2,6-diisopropylaniline, 2-tert-butylaniline, aniline, and the like.

Preferably, the aromatic amine is a mononuclear aromatic amine and is substituted in at least one ortho position with a lower alkyl group. These include o-toluidine, o-ethyl-aniline, o-isopropylaniline, o-tert-butylaniline, 2,6-dimethyl-aniline, 2-methyl-6-ethylaniline, 2,6-diethylaniline, 2-methyl-6-isopropylaniline, and the like. The more preferred aromatic amines are substituted in both ortho positions with a lower alkyl group. These compounds include 2,6-dimethylaniline, 2,6-diethylaniline, 2,6-diisopropylaniline, 2-methyl-6-ethyl-aniline, 2-methyl-6-isopropylaniline, 2-ethyl-6-isopropylaniline, 2-methyl-6-tert-butylaniline, 2-methyl-6-sec-butylaniline, 2,6-di-sec-butylaniline and the like.

The amount of dimethylsulfoxide should be an amount which results in a satisfactory yield. About 0.9-20 moles of dimethylsulfoxide per mole of aromatic amine is a useful range. A preferred range is about 1-10 moles of dimethylsulfoxide per mole of aromatic amine.

Although not required, solvents may be included in the reaction. Examples of these are diethylcarbonate, toluene, xylene, chlorobenzene, heptane, 1,2-dimethoxyethane and the like.

Good results are achieved using about 0.8-2 moles of HCl per mole of aromatic amine. Preferably an equal mole amount of HCl is used. In a most preferred embodiment the aromatic amine is used in the form of its hydrochloride salt.

The reaction proceeds over a wide temperature range. A useful range is about 50°-200° C. A preferred range is about 100°-150 ° C.

The reaction is preferably carried out by stirring a solution or suspension of the aromatic amine hydrochloride in a solvent such as toluene or diethyl carbonate at about 100°-150° C. and adding dimethylsulfoxide to the stirred mixture.

The following examples illustrate how the reaction is carried out.

EXAMPLE 1

In a reaction vessel was placed 2 gms (0.01 mole) of 2,6-dimethylaniline hydrochloride and 30 gms of diethyl carbonate. The stirred mixture was heated to 124° C. at which time 15 ml dimethylsulfoxide was added. The suspension turned to a clear purple solution following which a crystalline precipitate formed. The diethyl carbonate was distilled out under vacuum at 80° C. and then aqueous caustic was added in an amount which made the mixture alkaline. The mixture was then extracted with 40 ml of toluene. The toluene extract was water washed and then the toluene was distilled out leaving a residue. This residue was distilled using a Kugel-rohr distillation set-up. The fraction removed at about 170° C. was crystallized from isporopanol yielding 4,4'-methylenebis-(2,6-dimethylaniline), mp 119-120° C.

EXAMPLE 2

In a reaction vessel was placed 10.7 gms (0.05 mole) of 2,6-diisopropylaniline hydrochloride and 150 ml diethyl carbonate. The stirred mixture was heated to 125° C. and then 7.1 ml of dimethylsulfoxide was added over a 30-minute period. The solvents dissolved and the solution turned purple. Heating was continued for 30 minutes. Crystalline solids formed and were filtered off and identified by NMR as the hydrochloride salt of 4,4'-methylenebis-(2,6-diisopropylaniline). Heating of the filtrate at 125° C. was continued for one hour. This liquid was then analyzed by VPC and found to contain 15.1% 2,6-diisopropylaniline, 1.8% unidentified product and 77.1% of 4,4'-methylenebis-(2,6-diisopropylaniline).

EXAMPLE 3

In a reaction vessel was placed 9.3 gms (0.05 mole) of 2,6-diethylaniline hydrochloride and 100 ml of diethyl carbonate. The mixture was stirred and heated under nitrogen to 125° C. Then 150 ml dimethylsulfoxide was added over a 50-minute period. The color changed from beige to pink. Stirring was continued at 125° C. for 2.5 hours. Reaction composition was monitored by VPC. After 90 minutes the 2,6-diethylaniline was completely converted to 4,4'-methylenebis-(2,6-diethylaniline).

I claim:

1. A process for making a methylenebisaniline, said process comprising reacting an aromatic amine having an unsubstituted ortho or para position with hydrogen chloride and dimethylsulfoxide.

2. A process of claim 1 wherein said hydrogen chloride is added to said aromatic amine to form an aniline hydrochloride and reacting said aniline hydrochloride with dimethylsulfoxide.

3. A process of claim 1 wherein said aromatic amine and dimethylsulfoxide are first mixed and then hydrogen chloride is added to the mixture.

4. A process of claim 1 for making methylenebis-aniline wherein said aromatic amine is aniline.

5. A process of claim 1 for making 4,4'-methylenebis-(2,6-dimethylaniline) wherein said aromatic amine is 2,6-dimethylaniline.

6. A process of claim 1 for making 4,4'-methylenebis-(2,6-diethylaniline) wherein said aromatic amine is 2,6-diethylaniline.

7. A process of claim 1 for making 4,4'-methylenebis-(2,6-diisopropylaniline) wherein said aromatic amine is 2,6-diisopropylaniline.

* * * * *